(12) United States Patent
Grunewald et al.

(10) Patent No.: US 8,118,775 B2
(45) Date of Patent: Feb. 21, 2012

(54) DEFLECTABLE CATHETER WITH BONDED CENTER STRUT AND METHOD OF MANUFACTURE FOR SAME

(75) Inventors: Debby Grunewald, Los Angeles, CA (US); Irma Hill, LaVerne, CA (US); Thomas Selkee, Claremont, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 197 days.

(21) Appl. No.: 12/207,130

(22) Filed: Sep. 9, 2008

(65) Prior Publication Data
US 2010/0063441 A1    Mar. 11, 2010

(51) Int. Cl.
*A61M 37/00* (2006.01)
(52) U.S. Cl. .................................................. 604/95.04
(58) Field of Classification Search ............... 604/95.04
See application file for complete search history.

(56) References Cited

U.S. PATENT DOCUMENTS

| | | | |
|---|---|---|---|
| RE34,502 E | 1/1994 | Webster, Jr. | |
| 5,531,686 A * | 7/1996 | Lundquist et al. | 604/95.04 |
| 5,782,828 A * | 7/1998 | Chen et al. | 606/42 |
| 6,066,125 A | 5/2000 | Webster, Jr. | |
| 6,123,699 A | 9/2000 | Webster, Jr. | |
| 6,171,277 B1 | 1/2001 | Ponzi | |
| 6,183,463 B1 | 2/2001 | Webster, Jr. | |
| 6,198,974 B1 | 3/2001 | Webster, Jr. | |
| 6,500,144 B1 * | 12/2002 | Russell et al. | 604/95.01 |
| 6,500,167 B1 * | 12/2002 | Webster, Jr. | 604/528 |
| 6,585,718 B2 * | 7/2003 | Hayzelden et al. | 604/523 |
| 6,605,086 B2 * | 8/2003 | Hayzelden et al. | 606/41 |
| 6,829,497 B2 * | 12/2004 | Mogul | 600/374 |
| 7,077,823 B2 | 7/2006 | McDaniel | |
| 2002/0165461 A1 * | 11/2002 | Hayzelden et al. | 600/523 |
| 2003/0187389 A1 | 10/2003 | Morency et al. | |
| 2005/0209557 A1 * | 9/2005 | Carroll et al. | 604/95.04 |

FOREIGN PATENT DOCUMENTS

| EP | 1 690 564 | 8/2005 |
|---|---|---|
| WO | WO 2009/085470 | 7/2009 |

OTHER PUBLICATIONS

EP Search Report EP 09 25 2148 Dated Feb. 19, 2010.

* cited by examiner

*Primary Examiner* — Nicholas Lucchesi
*Assistant Examiner* — Diva Ranade
(74) *Attorney, Agent, or Firm* — William A. Schoneman

(57) ABSTRACT

A catheter for diagnosing or treating the vessels found within a body or body space includes a center strut that is bonded, preferably thermally, along its longitudinal axis with the thermoplastic tubular member within which it is housed. The tubular member preferably has three layers: an inner layer, a braided layer and an outer layer. The composite catheter is made using a process in which two half-cylinder shaped mandrels are placed on each side of the center strut while the strut is heated in order to cause the thermal bonding. The bonded center strut provides in-plane deflection and improved transfer of torque to the tip of the catheter.

24 Claims, 14 Drawing Sheets

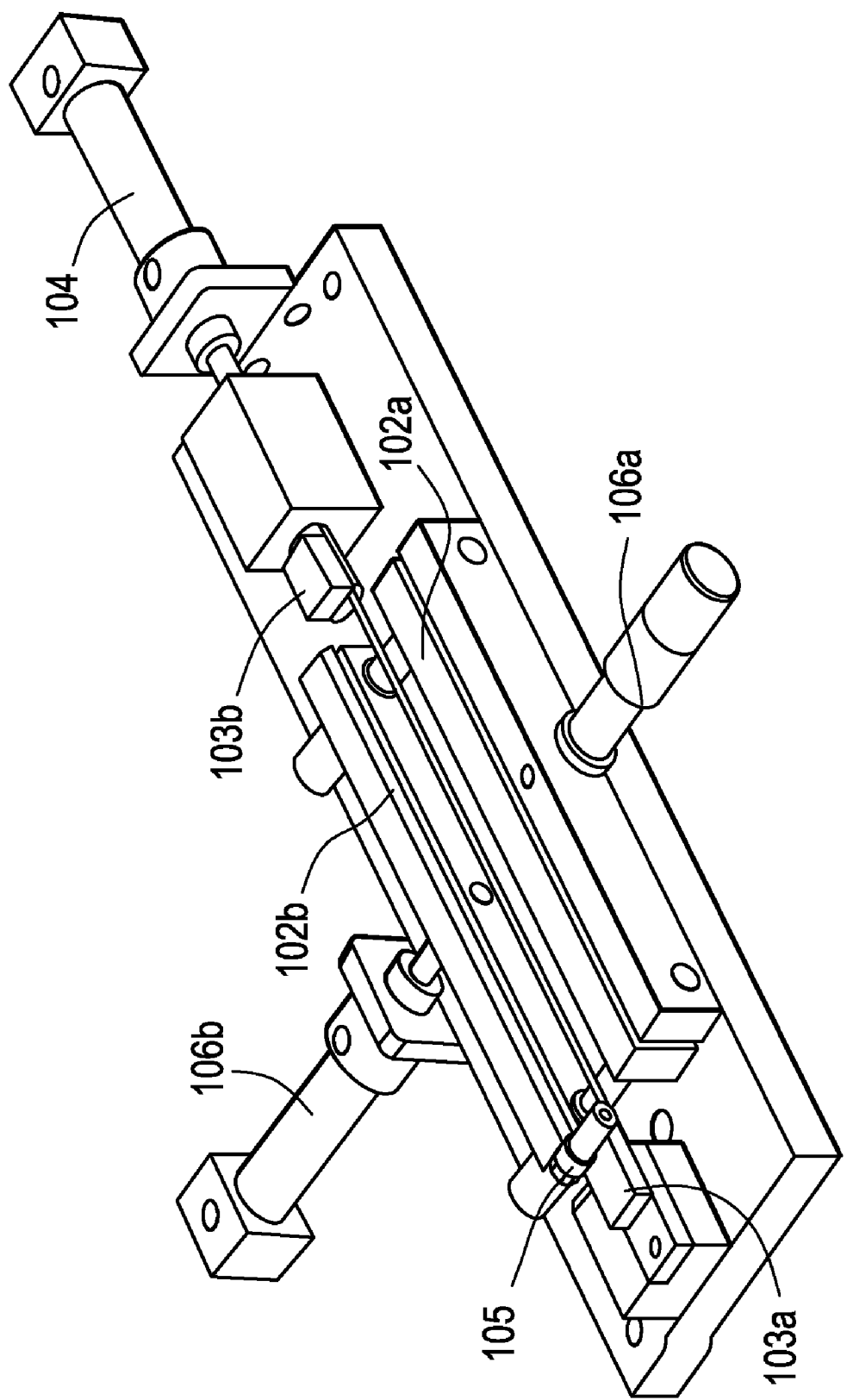

DEFLECTABLE CATHETER WITH BONDED CENTER STRUT AND METHOD OF MANUFACTURE FOR SAME

FIELD OF THE INVENTION

The present invention relates to a medical device for use in the vessel of a patient for the purpose of diagnosing or treating the patient, such as mapping tissue and/or ablating tissue using radio frequency (RF) or other sources of energy. More particularly, the invention relates to a deflectable catheter having a center strut bonded into the deflecting portion of the catheter tip to define an inseparable composite tip structure that maximizes the open internal volume of the catheter tip and the torsional rigidity of the catheter tip while minimizing the outside diameter of the catheter tip and providing uniform on-plane tip deflection. The invention also covers a method for making the same.

BACKGROUND OF THE INVENTION

Many abnormal medical conditions in humans and other mammals have been associated with disease and other aberrations along the lining or walls that define several different body spaces. In order to treat such abnormal conditions of the body spaces, medical device technologies adapted for delivering various therapies to the body spaces using the least invasive means possible.

As used herein, the term "body space," including derivatives thereof, is intended to mean any cavity within the body which is defined at least in part by a tissue wall. For example, the cardiac chambers, the uterus, the regions of the gastrointestinal tract, and the arterial or venous vessels are all considered illustrative examples of body spaces within the intended meaning.

The term "vessel," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of vessels within the intended meaning. Blood vessels are also herein considered vessels, including regions of the vascular tree between their branch points. More particularly, the pulmonary veins are vessels within the intended meaning, including the region of the pulmonary veins between the branched portions of their ostia along a left ventricle wall, although the wall tissue defining the ostia typically presents uniquely tapered lumenal shapes.

One means of treating body spaces in a minimally invasive manner is through the use of catheters to reach internal organs and vessels within a body space. Electrode or electrophysiology (EP) catheters have been in common use in medical practice for many years. They are used to stimulate and map electrical activity in the heart and to ablate sites of aberrant electrical activity. In use, the electrode catheter is inserted into a major vein or artery, e.g., the femoral artery, and then guided into the chamber of the heart that is of concern in order to perform an ablation procedure.

Steerable catheters are generally well-known. For example, U.S. Pat. No. RE 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter to the side wall of the catheter shaft. In this arrangement, lengthwise movement of the piston relative to the housing results in deflection of the catheter tip section. The design described in U.S. Pat. No. RE 34,502 is generally limited to a catheter having a single puller wire.

Bidirectional steerable catheters are also generally well known, as a variety of designs have been proposed. In many such designs, such as those described in U.S. Pat. Nos. 6,066,125, 6,123,699, 6,171,277, 6,183,463 and 6,198,974, a pair of puller wires extend through a lumen in the main portion of the catheter shaft and then into opposing off axis lumens in a deflectable tip section where the distal end of each puller wire is attached to the outer wall of the deflectable tip. Pulling one wire in a proximal direction causes the tip to deflect in the direction of the off axis lumen in which that wire is disposed.

In other designs, such as those described in U.S. Pat. No. 5,531,686, the puller wires are attached to opposite sides of a rectangular plate that is fixedly mounted at its proximal end and extends distally within a lumen in the tip section. In this arrangement, pulling one of the wires proximally causes the rectangular plate to bend in the direction of the side to which the pulled puller wire is attached, thereby causing the entire tip section to deflect.

In all of the designs for a steerable catheter, the method of manufacturing is generally complex, time-consuming and does not necessarily result in a catheter that accurately translates the longitudinal motion of the pull wire into uniform on-plane tip deflection.

SUMMARY OF THE INVENTION

The invention is directed to an improved steerable catheter, more particularly a bidirectional steerable catheter. The catheter comprises an elongated, tubular catheter body having at least one lumen extending therethrough and a deflectable tubular tip section having a center strut and two half-cylindrical lumens extending therethrough. The center strut is bonded, preferably thermally, to the interior of the tubular catheter substantially along the entire length of the center strut thereby creating an inseparable tip structure.

The catheter further comprises first and second puller wires having proximal and distal ends. Each puller wire extends from a control handle at the proximal end of the catheter body through a lumen in the catheter body and into one of the lumens in the tip section. The puller wires may be disposed in a tubular sleeve dimensioned so as to maintain the puller wires in close adjacent relationship. The distal ends of the puller wires are fixedly attached either to opposite sides of the center strut, to the tip electrode or the tubular structure of the distal tip section of the catheter.

The control handle includes a steering assembly having a lever arm carrying a pair of pulleys for drawing corresponding puller wires to deflect the tip section of the catheter. The pulleys are rotatably mounted on opposing portions of the lever arm such that one pulley is moved distally as the other pulley is moved proximally when the lever arm is rotated. Because each puller wire is trained on a respective pulley, rotation of the lever arm causes the pulley that is moved proximally to draw its puller wire to deflect the tip section in the direction of the off-axis lumen in which that puller wire extends.

Specifically, the present invention is a composite catheter tip comprising an extruded thin walled elastomeric tube spirally wrapped with a reinforcing braid wherein the elastomeric tube that has a center strut comprised of a thin elongated rectangular metallic strip where both thin longitudinal sides (edges) of the said strip are bonded, preferably thermally, to the inside wall of the elastomeric tube thereby creating a composite structure with inseparable members. The term "inseparable" is used to denote the creation of a composite structure between the elastomeric tube and the metallic strip so that any attempt to separate the elastomeric tube and metallic strip would cause irreversible destruction of the composite structure.

This composite tip structure provides two enclosed, large diametrically-opposed, half moon shaped lumens extending through the tip providing space for wiring, sensors, fluid carrying tubing and the like. The strut separating the half moon shaped lumens can be constructed from any of a number of superelastic (metallic) alloys such as nitinol, beta titanium or spring tempered stainless steel. This composite catheter tip design maximizes the cross-sectional area of the open lumens in the catheter tip and torsional rigidity of the catheter tip while minimizing the outer diameter of the catheter tip by providing a single uniform area moment of inertia at any cross section of the longitudinal axis of the catheter tip because the bonded center strut and elastomeric tube are not allowed to move with respect to each other during tip deflection. This composite structure provides uniform on-plane tip deflection and uniform torque and deflection forces regardless of the tip deflection angle because the tip cross-sectional area moment of inertia remains constant along the entire tip length during tip deflection. All known prior art tip designs exhibit varying cross-sectional area moments of inertia during tip deflection because the inner strut and outer elastomeric tube are fixed to each other only at their proximal and distal end locations and the strut and outer tube move with respect to each (other) during tip deflection. In all prior art designs, the combined centroidal axis of the independently moving strut and outer tube is continuously variable during tip curvature since the absolute distance between the centroidal axis of the whole (strut and outer tube) and the centroidal axis of each of the parts is variable. This produces non-uniform torque and deflection forces that are dependent on the degree of tip curvature.

The deflection curve profile of the catheter tip can be modified by varying the area moment of inertia of the strut cross section perpendicular to the struts longitudinal axis by utilizing cutting or coining operations that either remove material or change the material thickness in various portions of the center strut cross section. The composite deflecting tip with a bonded center strut has a large width to thickness ratio thus providing a first centroidal axis that has a large area moment of inertia and a second corresponding low area moment of inertia about a centroidal axis orthogonal to the first centroidal axis thereby providing exceptional on-plane deflection characteristics.

The method of the present invention results in a single unified high-performance composite structure for the deflecting tip assembly of a deflectable catheter that combines the properties of elastomers and metals and eliminates extruded core lumens. The two half-cylindrical lumens created by the bonded strut provide a large volume in which to place wiring, tip force and location sensors and tip irrigation lumens. Alternatively, an intermediate portion between the deflectable tip section and the tip electrode can be provided in which there is no center strut and which provides even greater room for temperature and location sensors. Catheter tip diameters can be reduced since the working volume of the tip lumen is maximized with this design.

In a preferred embodiment of the catheter an elongate tubular member having a proximal end and a distal end and having a lumen is thermally bonded to the longitudinal edges of a center strut that extends in the deflectable portion of the catheter. This bonding creates an inseparable composite structure from the elongate tubular member and the center strut.

A tip electrode is disposed at the distal end of the tubular member. A molded coupling has a distal portion adapted to receive a portion of the proximal end of the tip electrode and a proximal portion having at least one slot adapted to receive at least one of the first or second longitudinal edges of the center strut.

The distal end of the center strut comprises at least one snap-fit notch and the molded coupling further comprises at least one snap-fit wedge adapted to receive the snap-fit notch. This construction enables the rapid assembly of the tip electrode and the composite tubular member and center strut.

BRIEF DESCRIPTION OF THE DRAWINGS

FIG. 12 is a perspective view of a device for manufacturing the deflectable tip section of a catheter in accordance with the present invention.

DETAILED DESCRIPTION OF THE INVENTION

Figure 1A:
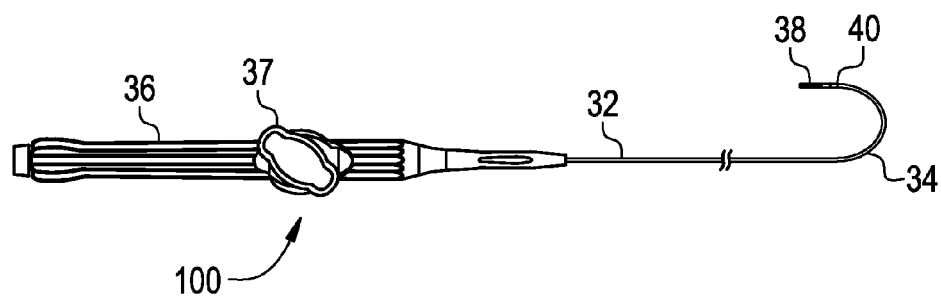
FIGS. 1A-C are a planar views of a deflectable EP catheter with rocker type deflection control handle in accordance with the present invention.
Figure 1B:
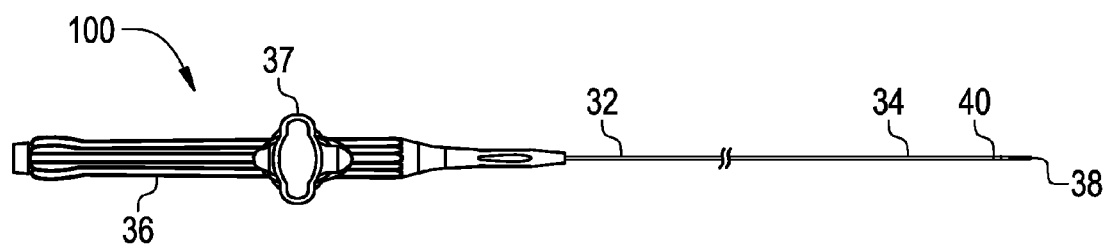
Figure 1C:
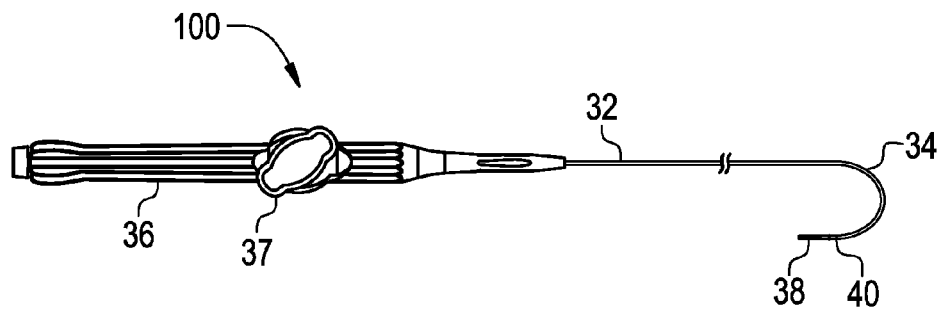

FIGS. 1A-C depict a planar view of an embodiment of a deflectable catheter in accordance with the present invention.

Figure 1D:
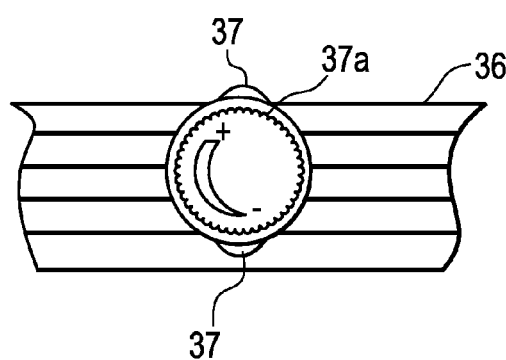
FIG. 1D is a planar view of the friction control knob located on the rocker type deflection control handle.

As shown in FIG. 1B, a preferred catheter 100 comprises an elongated tubular catheter body having a proximal section 32, a distal tip section 34 and a control handle 36 at the proximal end of the proximal section 32. Tip electrode 38 and optional ring electrode 40 are placed at or near deflectable distal tip section 34 so as to provide a source of ablation energy if the desired device is an RF ablation catheter or for receiving electrical signals if the catheter is a diagnostic EP mapping catheter. Control handle 36 may be one of many designs capable of placing a pulling force on puller wires used to deflect the deflectable tip section 34. Preferably, control handle 36 is the handle used in the Biosense EZ-Steer bidirectional family of products which control handle is depicted in FIGS. 1A-C. The "rocker" type lever 37 pulls one of two puller wires to deflect the catheter tip in one direction (FIG. 1A) then can alternatively select the second (opposite) puller wire to deflect the catheter tip in the other direction (FIG. 1C). The control handle 36 also had an adjustable friction control knob 37a shown in FIG. 1D that allows the operator to use the rocker lever 37 in a free state or to adjust the tension to lock the rocker level 37 and the deflected tip in place. The amount of friction in the movement of the rocker lever 37 increases as the friction control knob 37a is rotated clockwise until it reaches the fully locked position.

Figure 2:
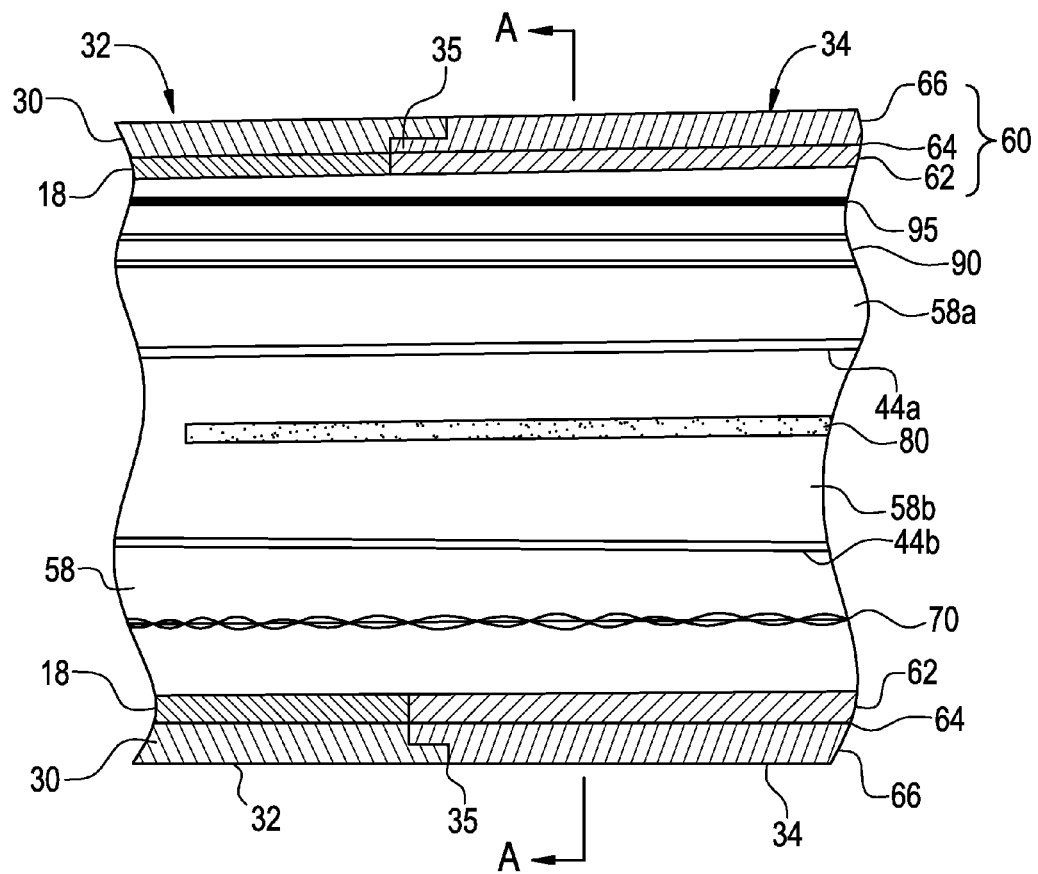
FIG. 2 is a longitudinal cross-sectional view of the deflectable distal tip section and a portion of the proximal section of the catheter of FIG. 1.
Figure 3:
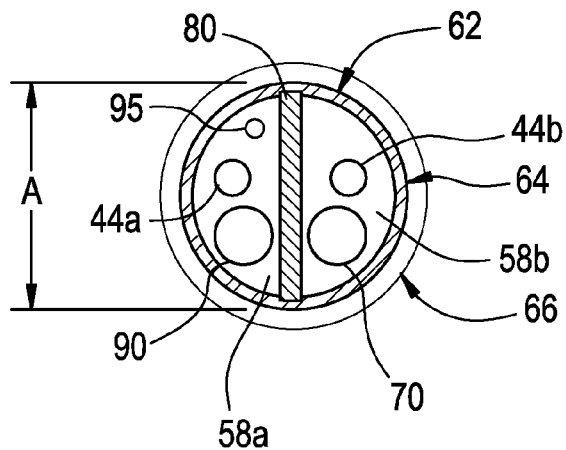
FIG. 3 is a cross-sectional view of the tubular section of the EP catheter of FIG. 2 through line A-A.

FIG. 2 depicts a cross-sectional view of the transition from proximal section 32 and deflectable section 34 of catheter 100 taken perpendicular to the center strut 80 that forms a portion of the catheter and FIG. 3 depicts the cross-section of the catheter of FIG. 2 through line A-A. Catheter 100 comprises an elongated tubular construction having a central lumen 58 through the distal portion 32 and two half-cylindrical lumens 58a and 58b in the deflectable tip portion 34. The proximal section 32 is flexible but substantially non-compressible along its length. Proximal section 32 can be made of any suitable construction and made of any suitable material. The preferred construction comprises an outer wall 30 made of Pellethane or PEBAX and an optional inner wall 18. The outer wall 30 may also comprise an imbedded braided mesh of stainless steel or similar material to increase torsional stiffness so that when control handle 36 is rotated the distal send of proximal section 32 as well as the distal section 34 will rotate in a corresponding manner.

The overall length of the length of the catheter will vary according to its application for use but a preferred length is between approximately 90 and 120 cm and more preferably between approximately 100 and 110 cm. The outer diameter of the proximal section 32 is also a design characteristic that varies according to the application of the catheter but is preferably less than approximately 8 French (Fr). Optional inner wall 18 comprises a polymeric tube which may optionally be spirally-sliced and is sized so that the outer diameter is about the same size or slightly smaller than the inner diameter of outer wall 30 thereby providing additional stiffness which can be controlled by the pitch angle of the spiral slice.

In the embodiment shown, the distal section 34 and the proximal section 32 are separate structures that have been fixedly attached to each other. Proximal section 32 and distal section 34 may be attached using a polyurethane adhesive at the joint 35 between the two sections. Other means of attachment include joining the proximal and distal sections using heat to fuse the sections together.

In the EP catheter of the present invention, tip electrode 38 and optional ring electrodes 40 shown in FIGS. 1A-1C are each electrically connected to one of the bundle of lead wires 70. Each wire in the bundle of lead wire 70 extends from the control handle 36 through the lumen 58 in the proximal section 32 and through one of lumens 58a or 58b in distal section 34 to tip electrode 38 and optional ring electrode (or electrodes) 40. The proximal end of each lead wire 70 is connected to an appropriate connector (not shown) in the control handle 36 which can be connected to a suitable source of RF energy or to an EP mapping or other diagnostic or therapeutic system.

Figure 4:
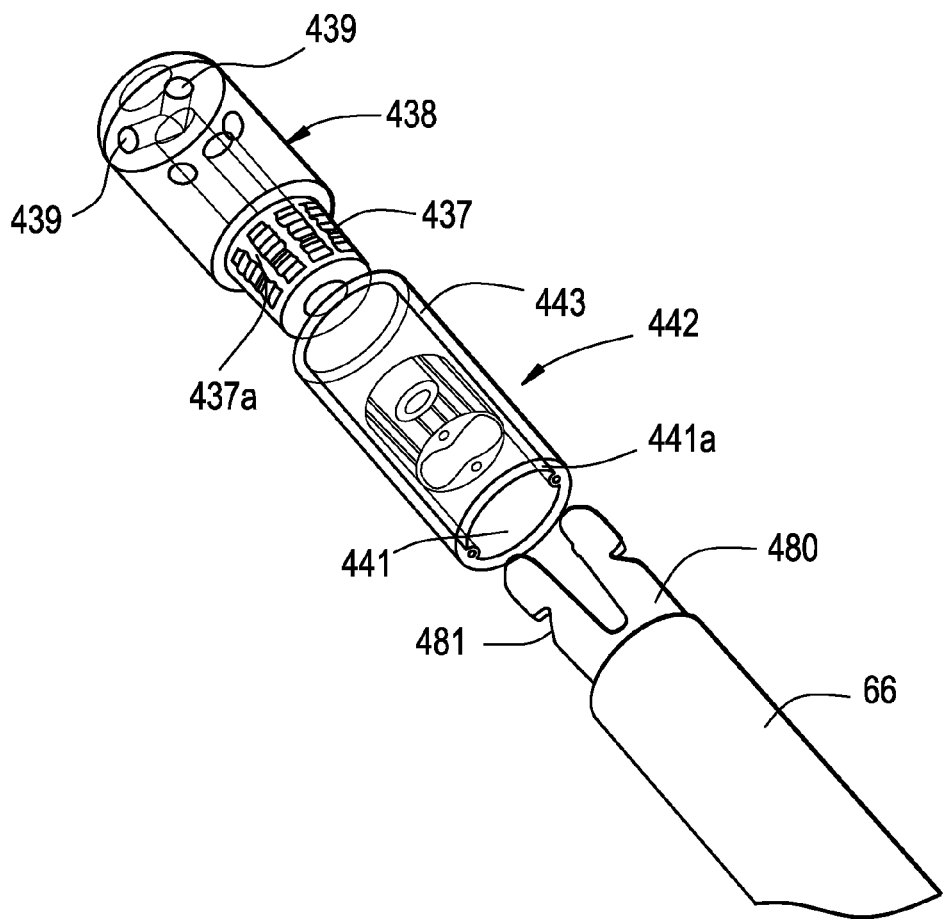
FIG. 4 is an exploded perspective view of the distal tip of an embodiment of a deflectable catheter in accordance with the present invention.
Figure 5:
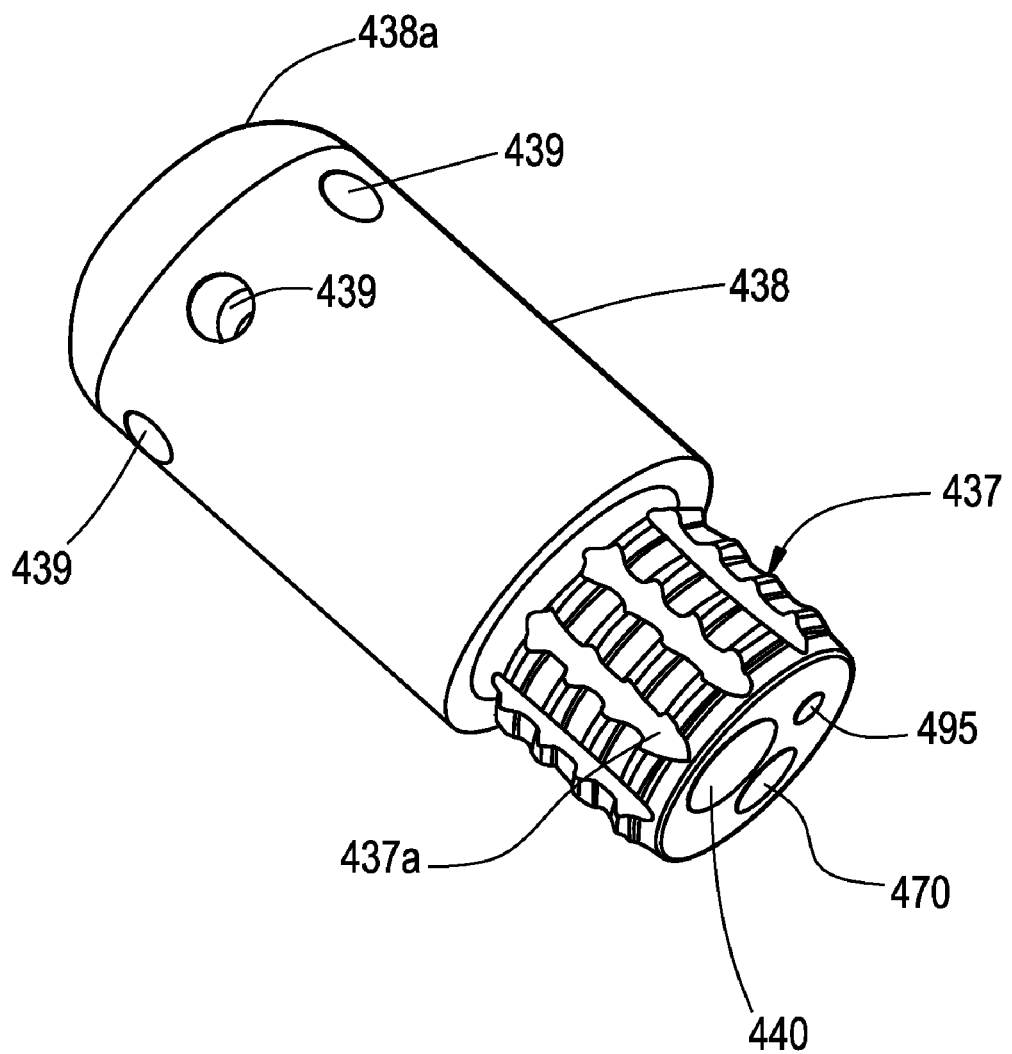
FIG. 5 is a perspective view of a tip electrode of the deflectable tip section of a catheter in accordance with the present invention.

Irrigation lumen 90 provides a conduit for transporting fluid from the proximal end of the catheter to the distal tip portion 34. Irrigation lumen 90 is in fluid communication with one or more fluid ports in the tip electrode 38. FIGS. 4 and 5 depict on possible arrangement of irrigation fluid ports 439 in a tip electrode. Irrigation lumen 90 is used to transport an irrigation fluid through the catheter and out through the fluid ports in the tip in order to reduce coagulation of bodily fluids such as blood at or near the tip electrode.

In a bidirectional catheter a pair of puller wires 44a and 44b extend through the through lumen 58 in the proximal section 32 and each extend through one of lumens 58a and 58b in distal section 34. The puller wires are made of any suitable material such as stainless steel or Nitinol wire or a non-metallic yarn such as Vectran® material. Preferably, each puller wire 44 is covered with a lubricious coating such as PTFE or a similar material. Each puller wire 44 extends from the control handle 36 to near the tip of distal section 34.

A sleeve or sleeves (not shown) may be used to house the puller wires proximally to the soft tip of the catheter. The sleeve is used to keep each puller wire on its respective sides of the center strut. For bi-directional deflection the opposing puller wires will always be placed in a separate lumen. With this design placing multiple puller wires in one lumen would be used for achieving different deflection curves in one deflection direction. Such a sleeve may be made of any suitable material, e.g., polyamide or polyimide.

Examples of other suitable control handles 36 that can be used with the present invention are described in U.S. Pat. Nos. 6,123,699, 6,171,277, 6,183,463 and 6,198,974 the disclosures of which are hereby incorporated by reference. In such control handles proximal movement of the thumb control relative to the handle housing results in proximal movement of the first piston and first puller wire relative to the handle housing and catheter body, which results in deflection of the tip section in the direction of the lumen into which the first puller wire extends. Distal movement of the thumb control relative to the handle housing results in distal movement of the first piston, causing proximal movement of the second piston and puller wire relative to the handle housing and catheter body, which results in deflection of the tip section in the direction of the lumen into which the second puller wire extends. Additional configurations of puller wires 44 and gearing within the control handle may be used such as those disclosed in U.S. Pat. No. 7,077,823 which is also hereby incorporated by reference.

The distal section 34 is comprised of an inner layer 62, braid layer 64 and outer layer 66 of the distal tip section described in greater detail below with respect to the method of manufacturing the catheter of the present invention discussed below with reference to FIG. 12.

Additionally, a safety wire 95 may be used to secure the tip electrode to the catheter shaft so as to prevent detachment of the tip electrode. The safety wire is preferably a 0.0065 inch diameter monel which is routed through the lumen 58 in the proximal portion 32 of the catheter as well as through one of the two lumens 58a or 58b in the distal tip portion 34. The distal end of the safety wire is attached to the tip electrode 38 while the proximal portion is attached to an anchor point inside the control handle 36.

FIG. 4 depicts an exploded view of the distal tip of a deflectable catheter in accordance with the present invention. FIG. 5 is a perspective view of tip electrode 438. Tip electrode 438 depicted in FIGS. 4 and 5 is a machined metallic electrode comprised of a metal that is non-reactive in bodily fluid such as of gold, platinum, palladium or an alloy thereof. Tip electrode 438 may also be made of a first metal such as copper, silver, gold, aluminum, beryllium, bronze, palladium or alloys thereof which is then plated either internally and/or externally with a non-reactive metal such as gold, platinum, palladium or an alloy thereof. Tip electrode 438 may include a plurality of irrigation ports 439 connected to a central irrigation lumen 440 although such ports and lumens are optional. The proximal end of tip electrode 438 comprises a base 437 having a smaller diameter than the remainder of the tip electrode and adapted to fit coupling 442. Base 437 may include a plurality of serrations 437a that improve the bonding of tip electrode 438 into coupling 442. Base 437 of the tip electrode 438 is heat bonded or ultrasonically welded to the coupling 442. Tip dome 438a may be machined to provide a rounded atraumatic distal tip in order to reduce tissue damage during placement and/or use of the catheter. Lumen 495 provides a passageway for safety wire 95 and lumen 470 provides a passageway for lead wire 70 that provide energy to the tip electrode 438. Lead wire 70 is attached to tip electrode 438 using an electrically conductive solder or epoxy.

Figure 6:
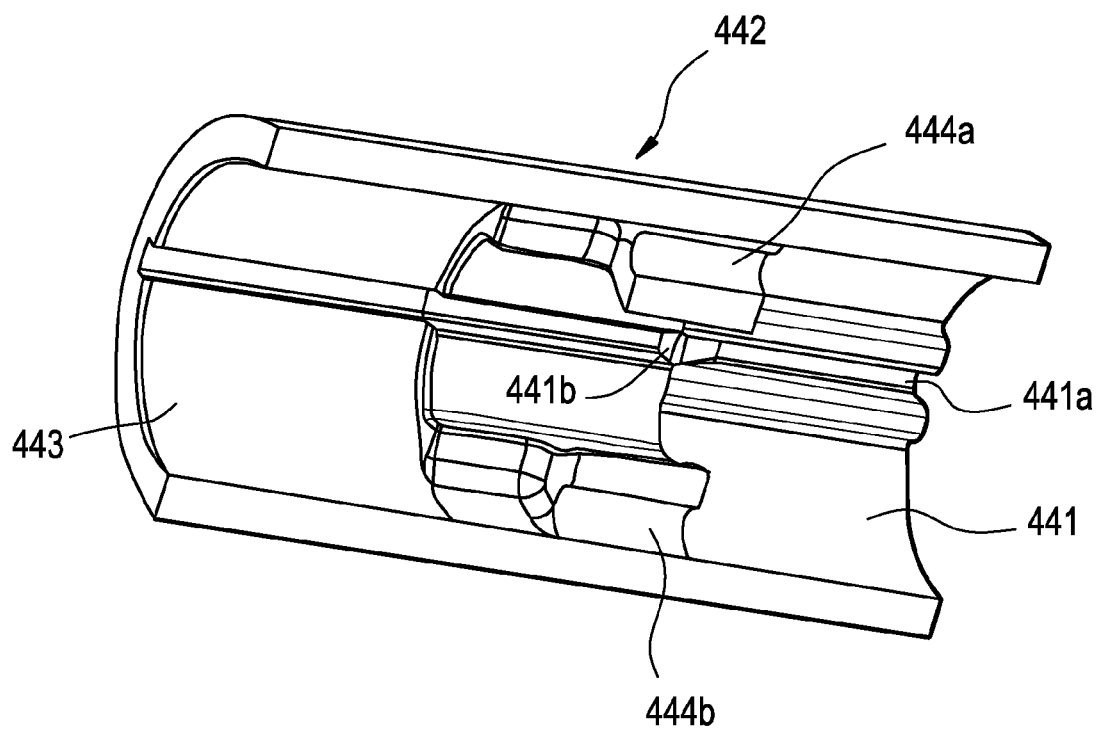
FIG. 6 is a cross-sectional perspective view of a molded coupling of the deflectable tip section of a catheter in accordance with the present invention.
Figure 7A:
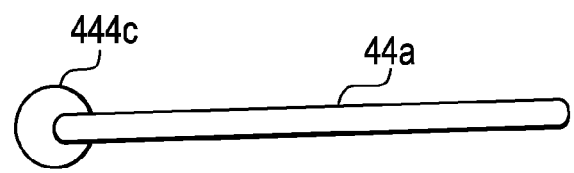
FIG. 7a is a planar view of a puller wire for use in the deflectable tip section of a catheter in accordance with the present invention.

Injection molded coupling 442 depicted in FIGS. 4 and 6 has a distal section 443 with an internal diameter at its distal end adapted to receive the base 437 of tip electrode 438 and has a proximal section 441 with a slot 441a adapted to receive the distal end 480 of the center strut 80. Coupling 442 is injection molded from a medical grade polymer such as PEEK, ABS or Polycarbonate or other appropriate material known to one skilled in the art. Distal end 480 of center strut 80 also includes a snap-fit notch 481 adapted to lock over snap-fit wedge 441b in the coupling 442 thereby providing a mechanism for the quick assembly of the distal section of the deflectable catheter which method is described in greater detail below. Puller wire anchor holes 444a and 444b are lumens that are adapted to receive puller wires 44a and 44b. Puller wires adapted for this use are shown in FIG. 7A. Puller wires 44a and 44b for use in this embodiment are preferably made of Vectran® wire which has had a ball of epoxy 444c attached to its distal end. The Vectran® wire should be cleaned with alcohol and/or an ultrasonic bath before application of a ball of epoxy that is then cured under ultraviolet light. It is important that the epoxy be well fixed to the distal end of the puller wires 44a and 44b. Alternatively, the puller wire could be high strength stainless steel (304V) to which a ball is produced at one end using a high-speed laser melting process.

Figure 8:
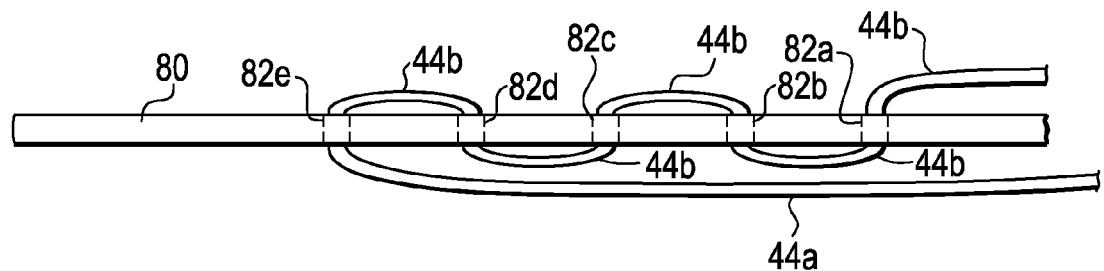
FIG. 8 is an elevational view of a center strut in accordance with a further embodiment the deflectable tip section of a catheter in accordance with the present invention.

A single puller wire 44, made of a non-metallic yarn such as Vectran® material, may be attached to the distal end of the catheter by threading the puller wire through one or more anchor holes 82a-e in center strut 80 so that the opposing ends of the puller wire, 44a and 44b, reside on opposing sides of the center strut as depicted in FIG. 8. Such anchor holes 82a-e in center strut 80 preferably have a diameter of 0.015 inch and are spaced apart by approximately 0.078 inch. Such anchor holes may be placed in the center strut 80 by laser cutting, punching and drilling. The number of holes on the strut, and the placement of the puller wires in one or more anchor holes 82a-e will alter the curve shape and allow for both symmetric and asymmetric curve designs. For creating a symmetric curve the opposing ends of the puller wires would exit the same anchor hole towards opposing sides of the strut. Means for changing curve shape can be controlled by the distance between anchor holes used for the opposing ends of the puller wire. When the end of each of the pull wires 44a and 44b are attached to opposing sides of the center strut 80, pulling pull wire 44a or 44b in the proximal direction will cause the distal end of the catheter 100 to deflect in-plane in the direction of the off-axis lumen in which the respective puller wire extends.

An alternate embodiment (not shown) uses two puller wires with metallic ferrules or plastic slugs to constrain the puller wires in their respective anchor hole located in the center strut. The puller wire would be threaded through the center strut on one side using the ferrule as a constraint from pulling completely through the anchor hole. An additional method for anchoring the puller wires is soldering, welding or using an adhesive to attach them to the center strut.

Figure 9:
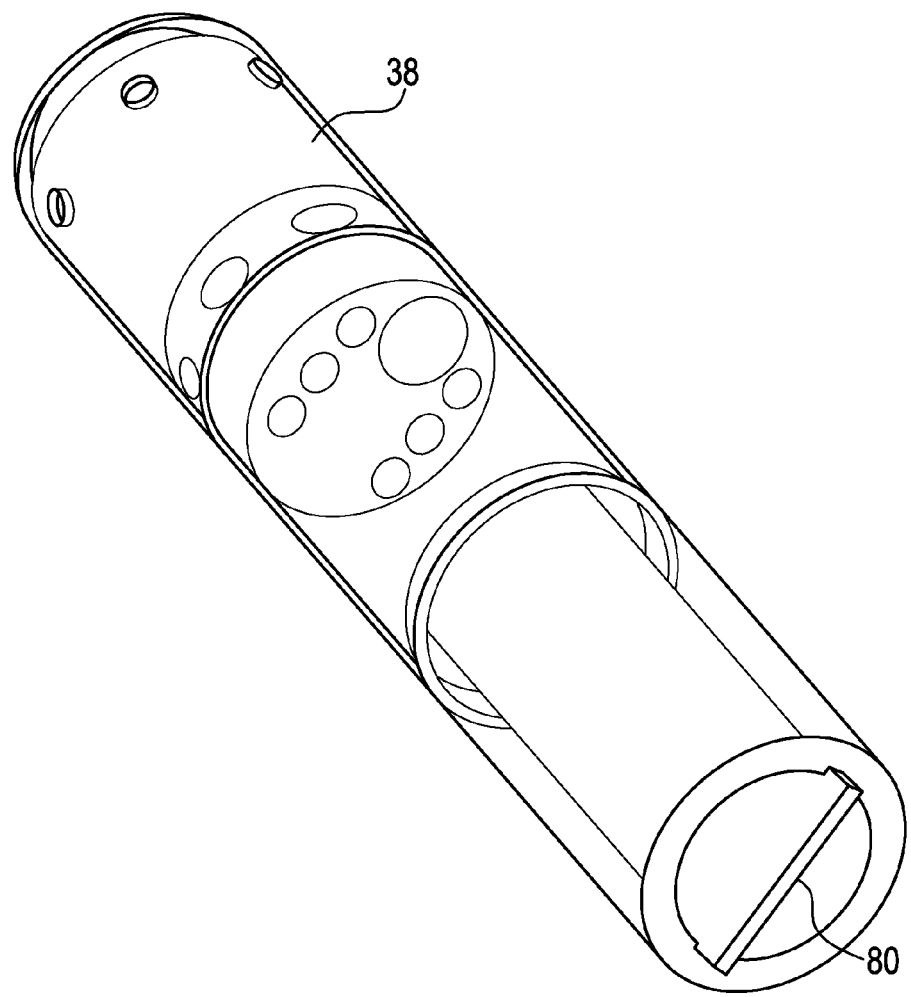
FIG. 9 is a perspective view of the device for manufacturing the deflectable tip section of a catheter in accordance with the present invention.
Figure 10:
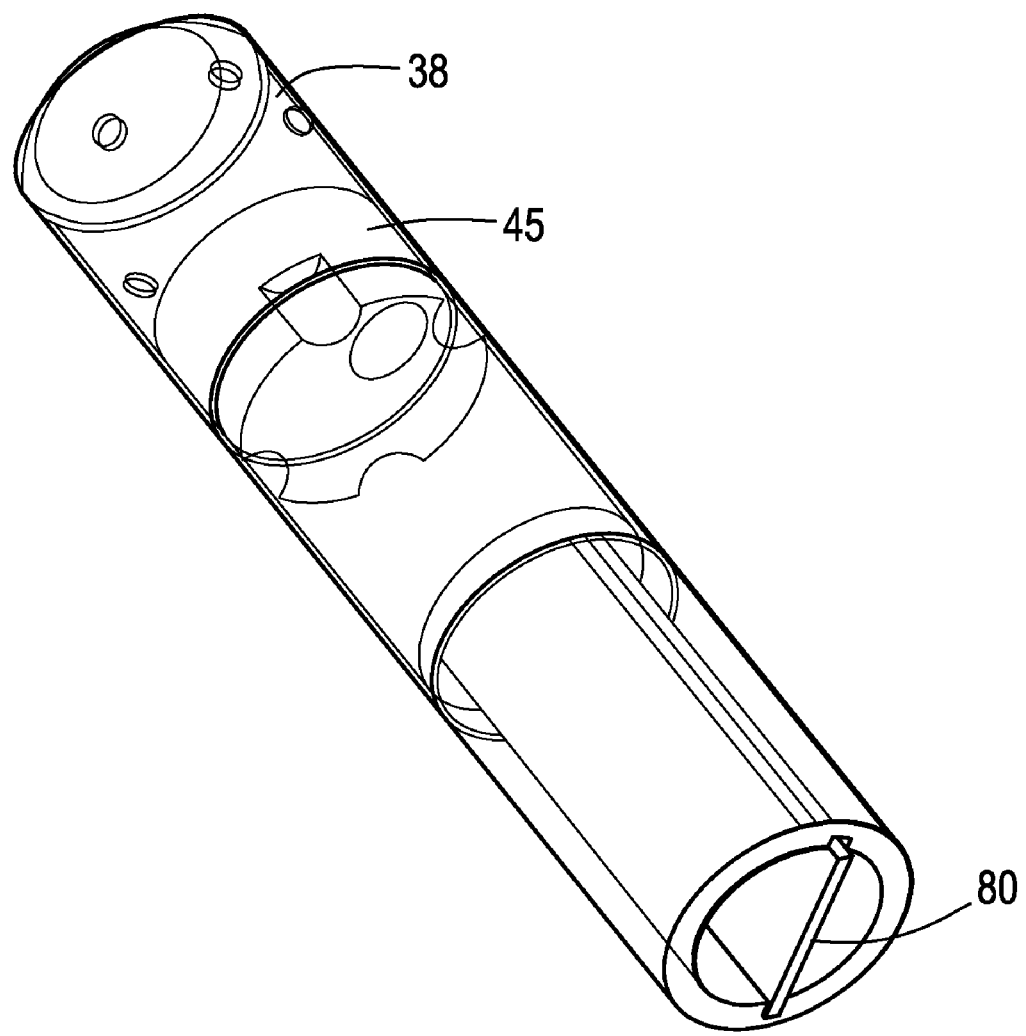
FIG. 10 is a perspective view of the distal tip of a deflectable catheter in accordance with the present invention.
Figure 11:
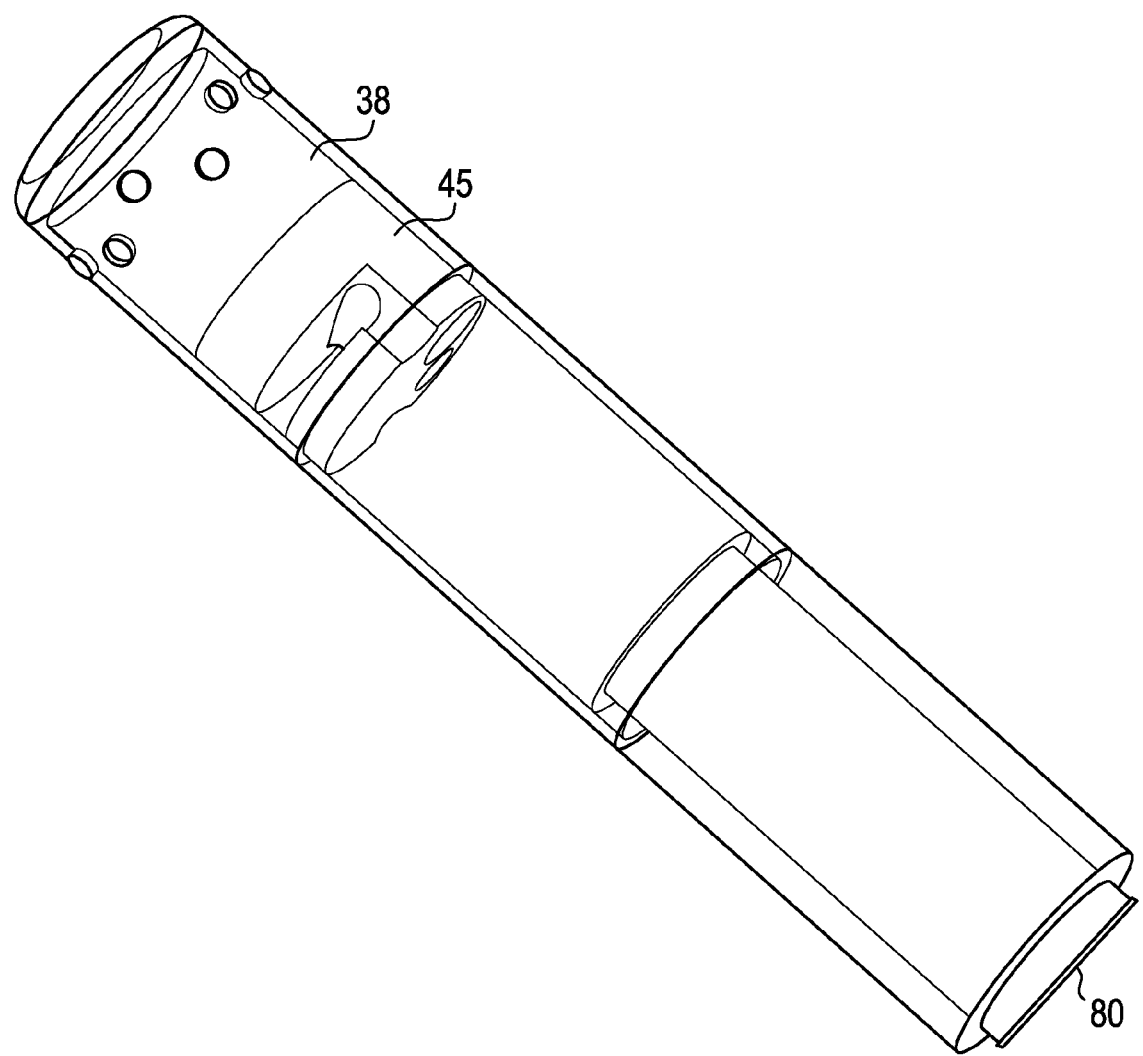
FIG. 11 is a perspective view of the distal tip of a deflectable catheter in accordance with the present invention.

Alternatively, the puller wires do not need to be attached to the center strut. A puller wire or puller wires could be attached to the tip dome or the distal end of the catheter's soft deflectable tip section. FIGS. 9-11 show multiple configurations of tip electrodes 38 that are adapted to receive a single puller wire 44. The single puller wire 44 connected to the tip electrode 38 provides bi-directional control. To achieve this, a single puller wire is threaded through the dome electrode with the opposite sides of the puller wire residing on opposite sides of the center strut. Deflection direction will correspond with the path of least resistance. Moreover, individually manipulating a puller wire will result in in-plane deflection in the direction of the off-axis lumen in which the respective puller wire extends. Such embodiment directly supports symmetric curve designs.

FIGS. 10 and 11 depict hollow tip electrodes 38 that are adapted to receive a plug 45 which is force fit into the hollow dome. Puller wire 44 is threaded through the plug. One or more puller wires may be anchored in this manner. The puller wire is constrained in place once the plug is appropriately placed in the tip electrode.

Figure 7B:
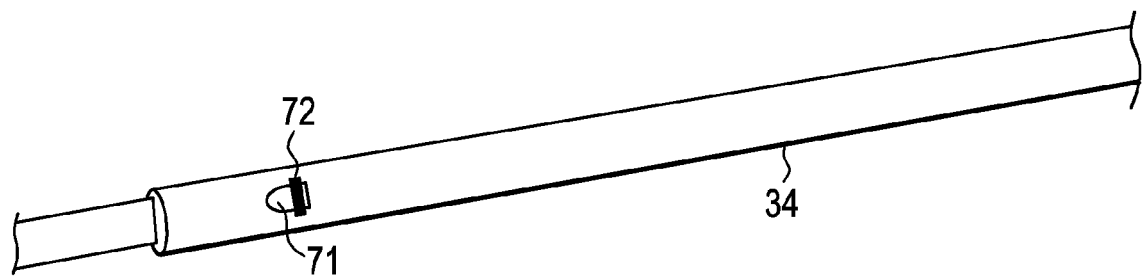
FIG. 7b is a perspective view of the distal section of a deflectable catheter in accordance with the present invention.

FIG. 7B depicts another embodiment of the distal tip section of the catheter 100 where the puller wires are attached to the side wall of the distal tip section 34 of catheter 100. A small hole 71 is drilled through the inner layer 62, braid layer 64 and outer layer 66 of the distal tip section. After the hole 71 is drilled, a grinder is used to lightly reduce the outer profile around the hole by removing approximately length=0.04" depth=0.013" of material. A stainless steel puller wire bar 72 is attached to the distal end of the puller wire 44 via crimping to a ferrule or other means of adhesion. When the puller wire 44 is brought through the anchor window the bar rests on the outer profile of the thermoplastic soft deflectable tip section. Polyurethane is used to pot over the puller wire bar 72 thereby rebuilding the original profile of the distal tip section 34. In this manner each puller wire may be anchored to the outer periphery of the catheter 100 at any location along the longitudinal axis of the distal tip section 34. It is possible to anchor multiple puller wires in this manner, each on opposing sides of the center strut. Changing the location of the anchoring location changes the deflection profile of the catheter.

The proximal end of the center strut 80 extends out of the proximal end of the soft deflectable tip portion. The proximal end of the center strut may be tapered so it can be readily placed within the proximal section 32 of the catheter helping to support the transition area. A sleeve preferably composed of PTFE may be placed over the tapered portion of the center strut constraining the puller wires and thereby preventing them from crossing. The sleeve is form fitting so it is tight around the center strut and wires but not so tight as to prevent the puller wires from readily moving in the longitudinal direction.

FIG. 12 depicts a device for manufacturing the distal tip section of the present invention. The inner layer 62 of the distal section 34 of a catheter in accordance with the present invention is produced by extruding a thin layer of a thermoplastic elastomeric material, preferably between 0.0025-0.0035 inch in thickness, over an acetyl polymer mandrel of the appropriate diameter. The inner layer 62 is then over-braided with a synthetic fiber braid layer 64 of approximately 0.002 to 0.003 inches in diameter. In a preferred embodiment the synthetic fiber is Pen monofilament from Biogeneral Advanced Fiber Technology. Next a second coat of elastomeric material is extruded over the braided inner layer to create the outer layer 66. The inner layer 62 and the outer layer 66 may be made from elastomers having the same shore hardness or from materials having different shore hardnesses. Preferably, the elastomer is PEBAX or Pellethane due to processability and high heat deflection temperatures.

After the outer layer 66 of elastomeric material is applied, the outside of the outer layer 66 is centerless ground to the desired finished outside diameter French size. The acetyl mandrel is removed and the center strut 80 is inserted through the center of the elastomeric tube 60. A half-moon elongated spacer made from a high temperature polymer such as PEEK, Teflon or liquid crystal polymer may be inserted into both sides of the inner diameter of the elastomeric tube 60 to stabilize and center the center strut 80 with respect to the center of the longitudinal axis of the elastomeric tube. This interim assembly is placed in the device depicted in FIG. 12.

Clamps 103a and 103b are used to clamp both longitudinal ends of the center strut 80. The clamps 103a and 103b of the device of FIG. 12 are constructed from an electrically conductive material such as copper. Clamp 103b retracts and puts the strut under controlled tension using a pneumatic push-pull cylinder 104 or alternate automatically controlled tensioning means. The interim assembly is then nested and constrained in two fixtures 102a and 102b having half-cylindrical indentations adapted to receive the assembly. Fixtures 102a and 102b when mated together by using fixture adjustment mechanism 106a and 106b place pressure on the interim assembly in order to limit localized heat distortion in the outside tip diameter. Fixtures 102a and 102b may be constructed from high heat transfer materials such as aluminum or copper. A proportional-integral-derivative (PID) temperature feedback loop controls electrical current introduced between the clamps 103a and 103b in order to heat the center strut 80 thereby causing the inner layer 62 inner diameter to thermally bond with both thin longitudinal sides of the center strut 80 to define a composite structure with inseparable members. The strut temperature is monitored using a temperature feedback sensor 105, preferably a non-contact, fast response time thermopile based infrared sensor that senses the strut surface temperature.

Figure 13A:
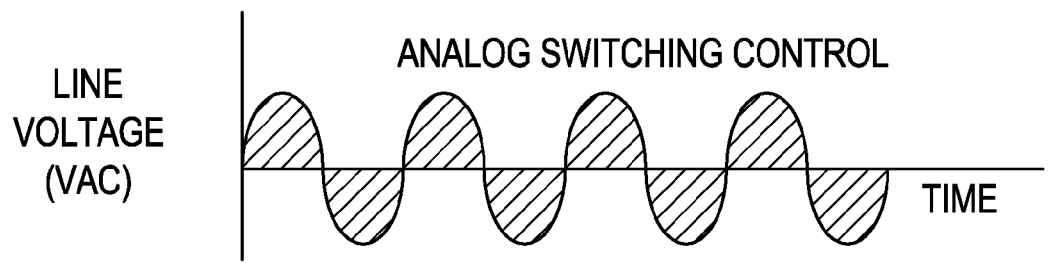
FIGS. 13A-D depict various control signals and a schematic for the control circuitry for use in the manufacture of a deflectable catheter in accordance with the present invention.
Figure 13B:
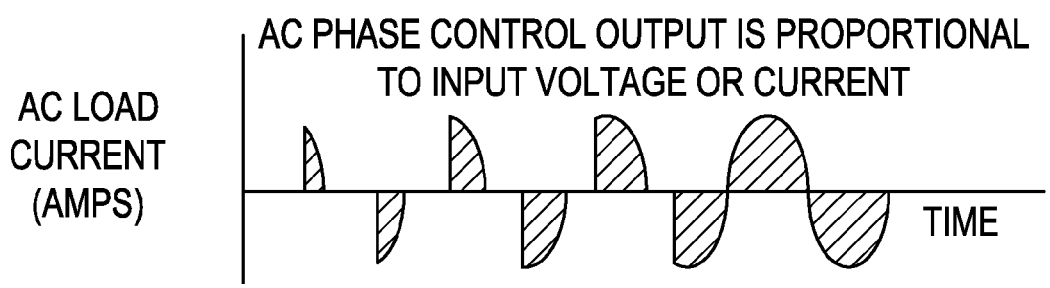
Figure 13C:
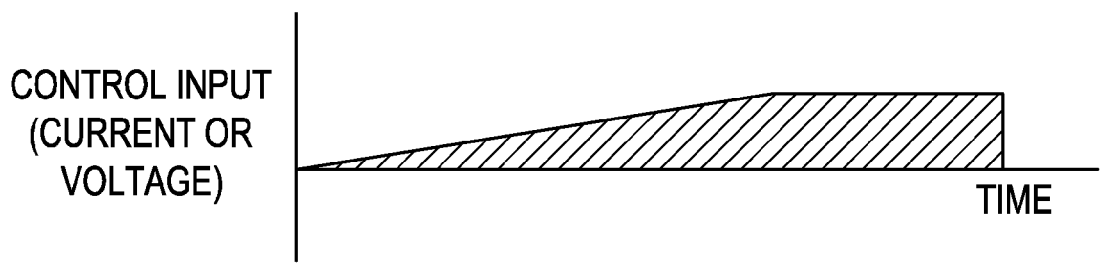
Figure 13D:
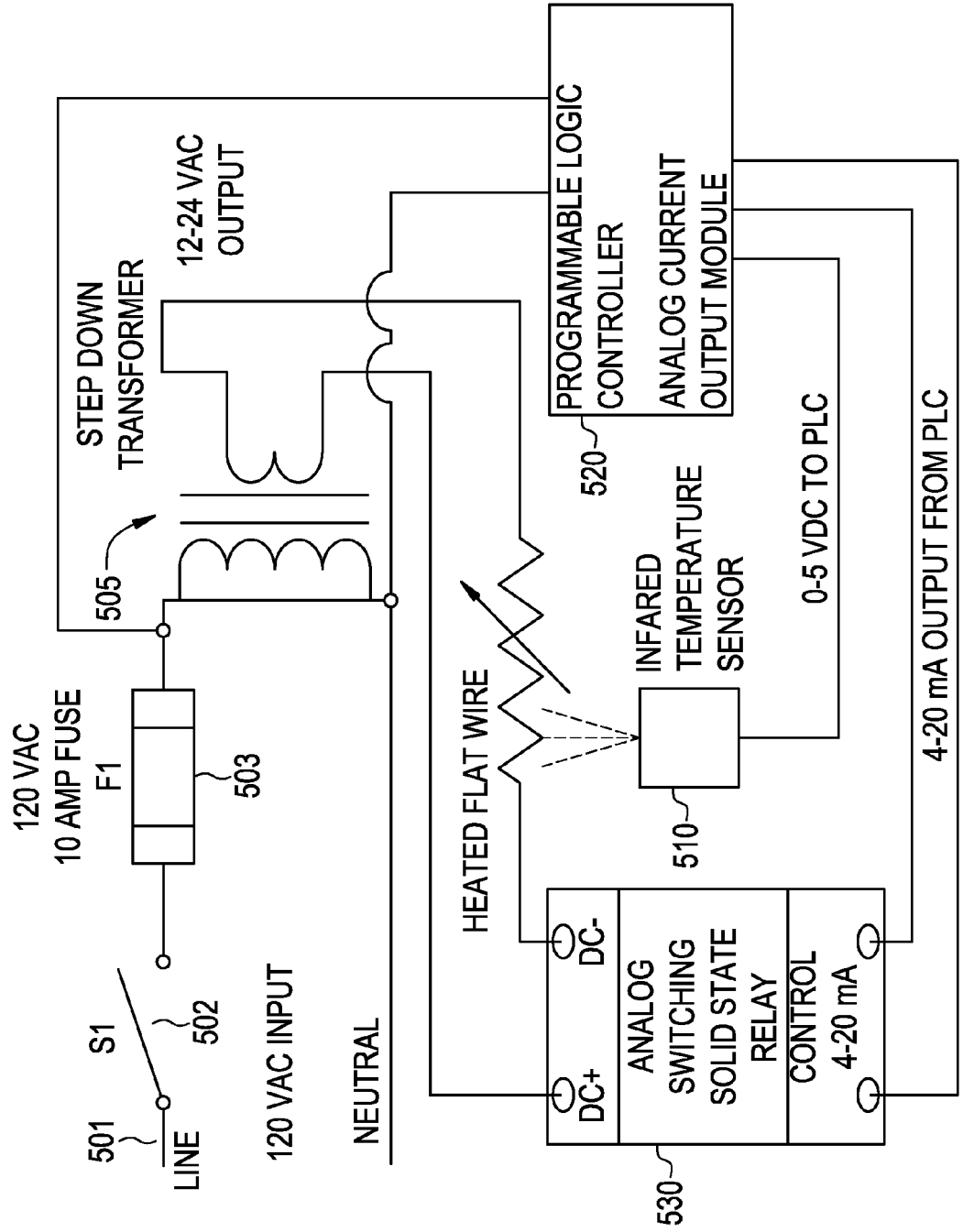

One method for heating the center strut using the device shown in FIG. 12 uses the feedback controlled power circuit depicted in FIG. 13D. An infrared temperature sensor 510 monitors the temperature of the heated center strut 80 and provides an input voltage to a programmable logic controller (PLC) 520 analog to digital converter module. The PLC 520 controls the analog switching solid state relay 530 with a built in synchronization circuit to control low-voltage, (5-28 VAC) 50-60 hertz alternating current by varying the phase-angle to rapidly heat the center strut 80. The proportional, integral, and derivative (PID) loop temperature feedback control by the PLC enables the strut temperature to be monitored and the PLC adjusts the phase angle accordingly to achieve the correct temperature set point. The line voltage, AC load current and control input to the analog switching solid state relay 530 can be seen in FIGS. 13A-C respectively. The circuit is powered by 120V AC line voltage 501 controlled by switch 502 and protected by 10 amp fuse 503 which is stepped down using transformer 505 resulting in 12-24 V AC output.

Figure 14A:
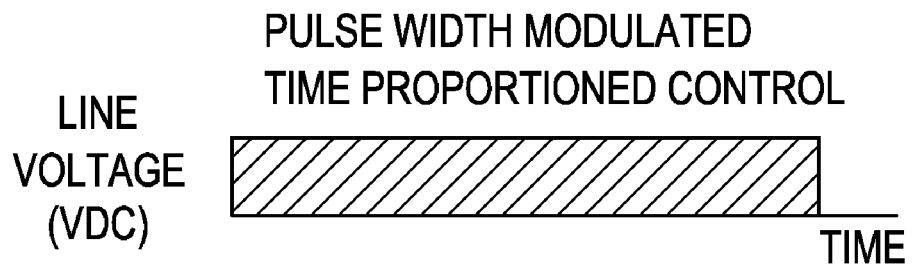
FIGS. 14A-D depict various control signals and a schematic for an alternative embodiment of the control circuitry for use in the manufacture of a deflectable catheter in accordance with the present invention.
Figure 14B:
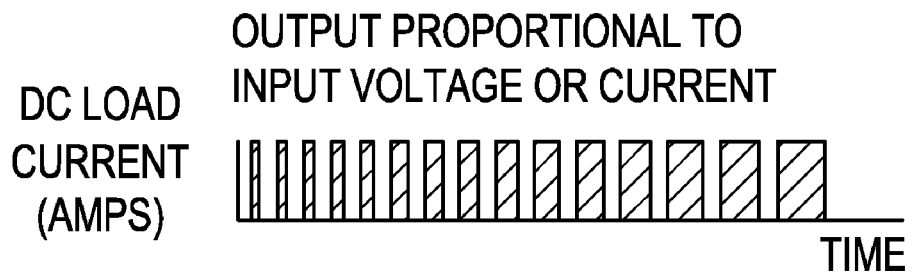
Figure 14C:
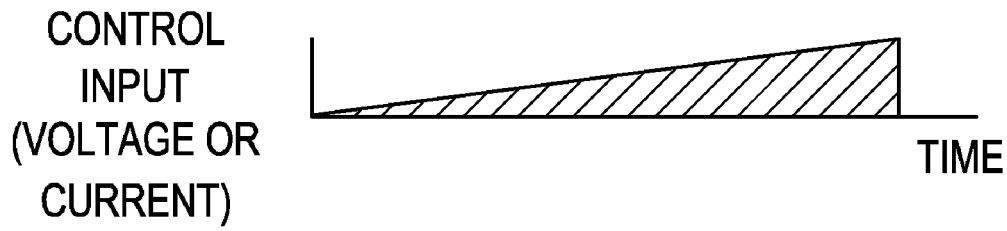
Figure 14D:
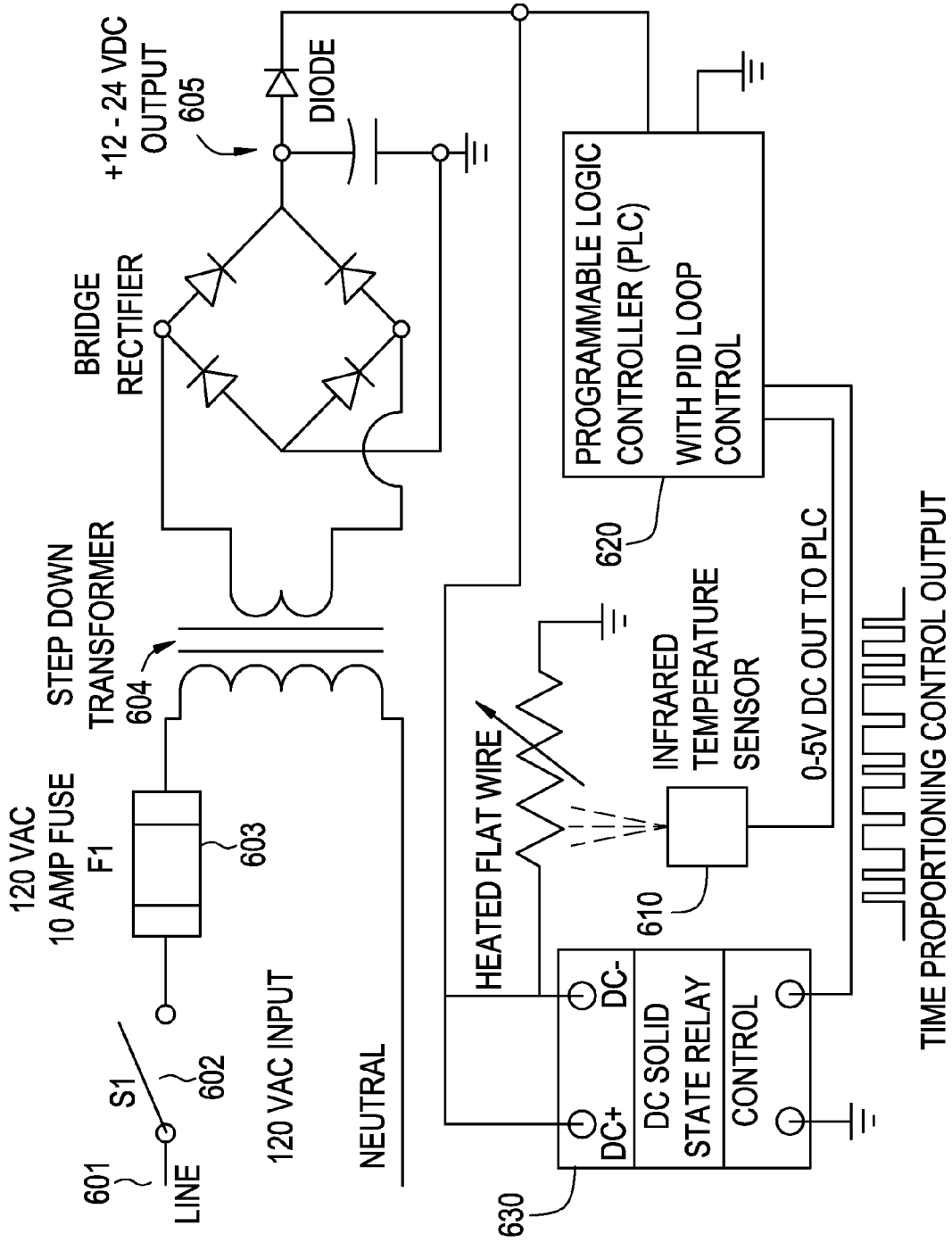

An alternate method for closed loop heating of the center strut is shown in FIGS. 14A-D. In the schematic of FIG. 14D for the heating power control circuitry, line voltage (120V AC) 601 controlled by switch 602 and protected by 10 amp fuse 603 is stepped down and converted into 12-24 V DC using step down transformer 604 and bridge rectifier 605. A direct current solid state relay 630 is used to rapidly switch (on-off) 5-24 volt direct current using a time proportioning control PID loop algorithm that controls the mosfet or transistor output of the programmable logic controller 620 to the solid state relay control side. The control output pulse width and duration is dependent on the analog temperature measurement feedback from the thermopile based infrared sensor 610 to the PLC.

Once heating is completed, the tension is removed from the from the strut by translating clamp 103a using the pneumatic push pull cylinder and the two halves of fixture 102a and 102b are retracted away from the assembly using fixture adjustment mechanisms 106a and 106b.

The distal tip section 34 with bonded center strut can then be affixed to the proximal section 32 as discussed above. The tip electrode 34 is affixed to the distal end of the distal tip section 34 and one of the lead wires 70 is attached to the electrode. A puller wire 44 or puller wires 44a and 44b are attached to the distal end using one of the arrangements discussed above. If the tip electrode contains fluid ports 39 then an irrigation lumen 90 is attached to the tip electrode and is routed through one of the two lumens.

One additional step in the manufacturing process is the roughening of side edges of the center strut 80 to create abrasions of approximately 250-500 micro inches to improve adhesion to the inner diameter of the elastomeric tube The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:
1. A catheter for use in a vessel comprising:
an elongate tubular member having a proximal end and a distal end and having a first lumen disposed therein;
a tip electrode disposed at the distal end of the tubular member;
a center strut extending from near the proximal end of the tip electrode through a deflectable distal portion of the elongate tubular member and having a first longitudinal edge and a second longitudinal edge;
wherein the center strut is bonded to the elongate tubular member along substantially the entire length of the first longitudinal edge and the second longitudinal edge to create an inseparable composite structure from the center strut and the elongate tubular member having a cross-sectional moment of inertia that remains substantially constant along the entire length of the composite structure.

2. The catheter of claim 1 wherein the center strut has been thermally bonded to the elongate tubular member along substantially the entire length of the first longitudinal edge and the second longitudinal edge.

3. The catheter of claim 1 further comprising a pull wire, having a proximal end and a distal end, for causing the deflectable distal portion of the elongate tubular member to deflect wherein the proximal end of the pull wire is attached to a control handle at the distal end of the catheter.

4. The catheter of claim 3 wherein the distal end of the pull wire is attached to the tip electrode.

5. The catheter of claim 1 further comprising a first pull wire and a second pull wire, each having a proximal end and a distal end, wherein the proximal end of the first and second pull wires are attached to a control handle and the distal end of the first pull wire is attached to a first face of the center strut and the distal end of the second pull wire is attached to the second face of the center strut.

6. The catheter of claim 5 wherein the center strut comprises at least one anchor hole for attachment of the distal ends of the first and second pull wires.

7. The catheter of claim 5 wherein the center strut comprises a plurality of anchor holes longitudinally spaced along the length of the center strut for attachment of the distal end of the first and second pull wires.

8. The catheter of claim 7 wherein the plurality of anchor holes are spaced from adjacent anchor holes by approximately 0.078 inch.

9. The catheter of claim 7 wherein the anchor holes are approximately 0.015 inch in diameter.

10. The catheter of claim 1 further comprising a first pull wire and a second pull wire each having a proximal end and a distal end, wherein the proximal ends of the first and second pull wires are attached to a control handle and the distal ends of the first and second pull wires are attached to the tip electrode.

11. The catheter of claim 10 wherein the tip electrode is comprised of a hollow portion and a plug and the distal ends of the first and second pull wires are attached to the plug prior to insertion in the hollow portion.

12. The catheter of claim 1 further comprising a temperature sensor.

13. The catheter of claim 1 further comprising a location sensor.

14. The catheter of claim 1 wherein the tip electrode has at least one irrigation port and the catheter further comprises an irrigation lumen in communication with the irrigation port.

15. The catheter of claim 14 wherein the tip electrode comprises a plurality of irrigation ports.

16. The catheter of claim 1 further comprising a first pull wire and a second pull wire each having a proximal end and a distal end, wherein the proximal ends of the first and second pull wires are attached to a control handle and the distal ends of the first and second pull wires are attached to anchors and are threaded through first and second holes in the tubular member.

17. The catheter of claim 1 wherein the tubular member has an inner layer, a braided layer and an outer layer along its entire length and wherein the first longitudinal edge and the second longitudinal edge of the center strut is thermally bonded to the inner layer of the tubular member along the entire length of the first longitudinal edge and the second longitudinal edge of the strut.

18. The catheter of claim 1 wherein the first and second longitudinal edges of the center strut comprise roughened areas to improve bonding with the tubular member.

19. The catheter of claim 1 further comprising a molded coupling adapted to receive the proximal end portion of the tip electrode.

20. The catheter of claim 19 wherein the distal end of the center strut comprises at least one snap-fit notch and the molded coupling further comprises at least one snap-fit wedge adapted to receive the snap-fit notch.

21. The catheter of claim 20 wherein the snap-fit notch and snap-fit wedge lock together in a one-way manner in order to secure the center strut in the molded coupling.

22. The catheter of claim 19 wherein the molded coupling further comprises at least one slot adapted to receive at least one of the first or second longitudinal edges of the distal portion of the center strut.

23. A catheter for use in a vessel comprising:
   an elongate tubular member having a proximal end and a distal end and having a first lumen disposed therein;
   a tip electrode disposed at the distal end of the tubular member;
   a center strut extending from near the proximal end of the tip electrode through a deflectable distal portion of the elongate tubular member and having a first longitudinal edge and a second longitudinal edge;
   a molded coupling having a distal portion adapted to receive a portion of the proximal end of the tip electrode and having a proximal portion having at least one slot adapted to receive at least one of the first or second longitudinal edges of the center strut;
   wherein the center strut is bonded to the elongate tubular member substantially along entire length of the first longitudinal edge and the second longitudinal edge to create an inseparable composite structure of the center strut and the elongate tubular member having a cross-sectional moment of inertia that remains substantially constant along the entire length of the composite structure.

24. The catheter of claim 23 wherein the distal end of the center strut comprises at least one snap-fit notch and the molded coupling further comprises at least one snap-fit wedge adapted to receive the snap-fit notch.

* * * * *